United States Patent [19]

Levine

[11] Patent Number: 5,707,876
[45] Date of Patent: Jan. 13, 1998

[54] METHOD AND APPARATUS FOR HARVESTING CONSTITUENT LAYERS FROM A CENTRIFUGED MATERIAL MIXTURE

[75] Inventor: Robert A. Levine, Guilford, Conn.

[73] Assignee: Stephen C. Wardlaw, Old Saybrook, Conn.

[21] Appl. No.: 621,787

[22] Filed: Mar. 25, 1996

[51] Int. Cl.[6] ........................ B01L 11/00
[52] U.S. Cl. .............. 436/177; 436/174; 436/180; 422/101; 422/102; 210/782; 210/789
[58] Field of Search ............... 436/174, 177, 436/180; 422/100, 101, 102; 210/782, 789, 516, 518

[56] References Cited

U.S. PATENT DOCUMENTS

| | | | |
|---|---|---|---|
| 3,291,693 | 12/1966 | Brown | 210/789 |
| 3,508,653 | 4/1970 | Coleman | 210/789 |
| 4,082,085 | 4/1978 | Wardlaw et al. | 128/2 G |
| 4,436,820 | 3/1984 | Reiter | 436/67 |
| 4,824,560 | 4/1989 | Alspector | 209/208 |
| 4,853,137 | 8/1989 | Ersson | 210/782 |
| 4,867,887 | 9/1989 | Smith | 210/782 |
| 5,019,243 | 5/1991 | McEwen et al. | 210/94 |
| 5,065,768 | 11/1991 | Coleman et al. | 128/760 |
| 5,163,582 | 11/1992 | Godolphin et al. | 222/1 |
| 5,236,604 | 8/1993 | Fiehler | 210/782 |
| 5,456,885 | 10/1995 | Coleman et al. | 422/101 |
| 5,560,830 | 10/1996 | Coleman et al. | 210/695 |

Primary Examiner—Long V. Le
Attorney, Agent, or Firm—William W. Jones

[57] ABSTRACT

Constituent layers are harvested from a centrifuged material mixture contained in a centrifuge tube assembly. The centrifuge tube assembly includes a transparent tube, one end of which is closed by an elastomeric cap. The tube contains one or more detectable constituent layer boundary markers which will settle gravimetrically in the material mixture when the latter is centrifuged. The markers will identify boundaries of the constituent layers which will gravimetrically separate from each other during the centrifugation step. After centrifugation, a cannula is inserted into the tube through the elastomeric cap, and a fluid material such as a liquid or a gas is injected into the tube through the cannula. The injected material displaces the centrifuged mixture column and the boundary markers toward the end of the tube opposite the cap, which opposite end is open so that the centrifuged material is expressed from the tube therethrough. The boundary markers allow stepwise expression or harvesting of gravimetrically identifiable constituent layers from the tube for further processing, testing or analysis.

7 Claims, 1 Drawing Sheet

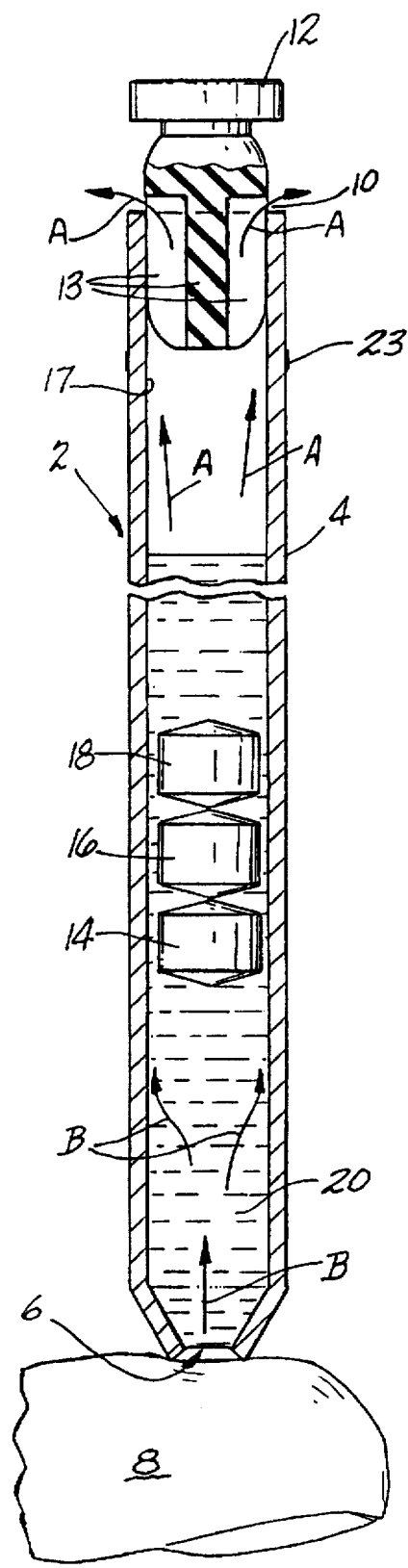
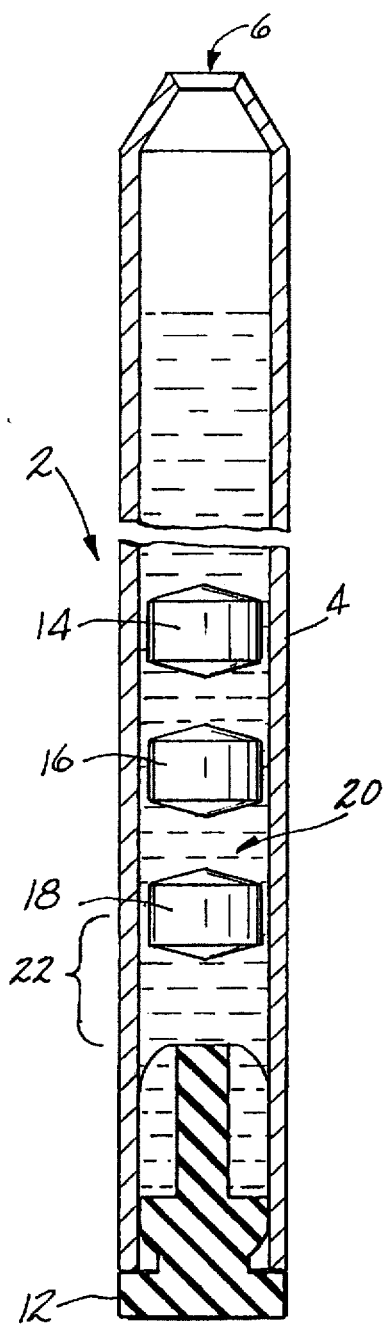
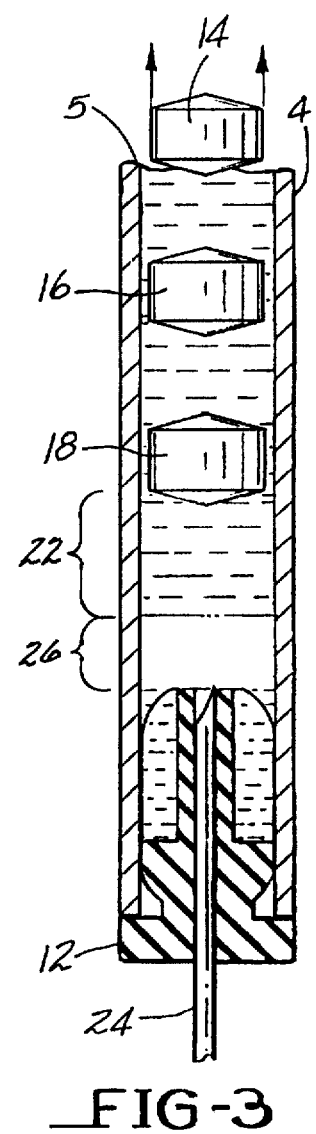
FIG-1
FIG-2
FIG-3

METHOD AND APPARATUS FOR HARVESTING CONSTITUENT LAYERS FROM A CENTRIFUGED MATERIAL MIXTURE

TECHNICAL FIELD

This invention relates to the harvesting of a constituent material layer from a multi-constituent mixture. More particularly, this invention relates to the inclusion of one or more markers which settle into the mixture when the latter is centrifuged to demarcate one or more interfaces between adjacent material layers so as to allow layers to be accurately defined and removed from a centrifugation vessel.

BACKGROUND ART

The removal of harvesting of constituent layers from a centrifugal multi-constituent mixture has application in many fields. The analysis of biological fluid constituents, such as blood components, for example, may involve the centrifugation of anti coagulated whole blood to separate formed components, i.e., the blood cells, from the non-formed component, i.e., the plasma. Typically, the centrifugation step will be performed in an evacuated tube such as the blood drawing tubes marketed by Becton Dickinson and Company under the trademark VACUTAINER®. The sample drawing and centrifugation tube typically contains a separator body which is formed from a plastic material having a specific gravity that will enable it to settle during the centrifugation step onto the top of the formed component layer in the blood sample. The separator prevents intermingling of the formed and unformed component fractions in the centrifuged blood sample, and it also stabilizes the centrifuged separation for further handling. After the centrifugation step, the plasma fraction is removed from the tube, usually by decanting from the centrifuged sample. U.S. Pat. Nos. 3,779,383 and 3,814,248, among others, disclose material layer harvesting methods and paraphernalia as generally described above.

U.S. Pat. No. 5,393,674 granted Feb. 28, 1995 to R. A. Levine, et al., discloses a method and paraphernalia for harvesting blood cells from a centrifugal sample of anti coagulated whole blood. The technique described in this patent involves the use of a hollow insert which is placed in the centrifuge tube with the blood sample. The insert is transparent and will move axially in the tube during the centrifugation step. The cells to be harvested from the tube will settle in the bore in the insert where they will layer out by specific gravity, and will elongate due to the restricted area they reside in. The cell layers can be differentiated by color, and can be removed from the centrifuge tube by being aspirated into a hypodermic syringe. The use of the aforesaid procedure for harvesting cells from a centrifuged sample of blood requires that the cells be stained so as to be distinguishable by cell type. Thus, the aforesaid procedure will not serve to separate and allow harvesting of red blood cells or other materials which cannot be differentially colored by the use of stains or other colorants. It would be desirable to provide a method and paraphernalia which is useful for identifying and harvesting constituent materials from a material mixture, which method and paraphernalia do not require the use of stains or other colorants to differentially color the constituents being harvested from the sample.

DISCLOSURE OF THE INVENTION

This invention relates to a method and paraphernalia for harvesting one or more constituent material layers from a centrifuged sample of a multi-constituent material. The sample is placed in a transparent tube which also contains one or more markers which are visible in the centrifuged sample. The markers are preferably discs which are formed from plastics with one or more predetermined densities. The markers can be formed from blends of plastics which have different densities. Thus, the density of the markers can be accurately and predictably controlled. Assuming that one practicing the invention knows the density of the constituent layer or layers that are to be harvested from the sample, then one or more markers with a density or densities which will indicate the border or borders of the layer or layers to be harvested will be employed.

For example, if one wanted to remove all layers of the sample that are heavier than a first predetermined density but lighter than a second predetermined density, two markers, one having the first predetermined density and another having the second predetermined density, will be placed in a centrifuge tube along with the sample to be centrifuged. When the sample is centrifuged, the layer to be harvested will be located between the two markers. Once the target layer or layers are located, a hypodermic is used to inject a fluid such as air or a sample-immiscible liquid into the centrifuge tube through a stoppered end thereof so as to force the centrifuged sample and the markers out of the tube through the opposite end thereof. The portion of the sample which is expressed from the tube between the two markers will be the target component layer. Thus, one performing the method of this invention can readily visually identify target component layers, and can therefore remove fractions of the sample from the tube which consist solely of the component layer or layers. It will be understood that using the technique of this invention, all of the material ejected from the tube between the time one marker is ejected and the time that the next adjacent marker is ejected will be a target sample component layer. Thus, any number of target component layers in a centrifuged sample can be harvested therefrom merely by adding an appropriate number of markers to the sample in the tube.

It is therefore an object of this invention to provide a method and paraphernalia for harvesting well-defined selected target constituent material layers from a centrifuged multi-constituent material sample.

It is a further object of this invention to provide a method and paraphernalia of the character described which involves the use of one or more discernible markers in the centrifuged sample, which markers define at least one boundary of the target constituent material layer or layers in the sample.

It is an additional object of this invention to provide a method and paraphernalia of the character described wherein the sample and markers are centrifuged in a transparent tube and, after centrifugation, the target layers are ejected from the tube along with the markers in the tube.

It is another object of this invention to provide a method and paraphernalia of the character described wherein the markers employed are discs formed from blends of plastics which impart controlled densities to the discs to enable the discs to gravimetrically settle into the boundary or boundaries of the target layers during centrifugation of the sample.

These and other objects and advantages of the invention will become more readily apparent from the following detailed description of a preferred embodiment of the invention, when taken in conjunction with the accompanying drawings, in which:

BRIEF DESCRIPTION OF THE DRAWINGS

FIG. 1 is a sectional view of a preferred embodiment of blood-drawing paraphernalia which employs the method of the invention to harvest target blood cell components from the blood sample;

FIG. 2 is a sectional view of the paraphernalia of FIG. 1 but showing the drawn blood sample after centrifugation thereof; and FIG. 3 is a sectional view similar to FIG. 2 showing the manner in which target blood cell layers are ejected from the blood sampling paraphernalia.

BEST MODE FOR CARRYING OUT THE INVENTION

Referring now to the drawings, there is shown in FIG. 1 a blood sampling assembly denoted generally by the numeral 2. The assembly 2 includes a capillary tube 4 which has a first crimped open end 6 which is adapted for drawing blood from a patient's finger 8 by means of a finger stick method. The opposite open end 10 of the tube 4 has fitted therein an elastomeric plug 12 which has radial flanges 13 that engage the tube bore wall 17 while providing gaps 20 through which air can escape from the tube 4 as indicated by arrows A. The tube 4 contains one or more marker bodies 14, 16, 18, etc., which are preferably disc-shaped as shown. The markers 14, 16, 18 are formed from plastics of progressively differing density, so that the marker closest to the crimped open end 6 of the tube 4 has the lowest density of the markers, and the marker closest to the plugged end 10 of the tube has the highest density of the markers. The intermediate markers will have densities that change step wise. The markers 14, 16, 18, etc., must therefore be placed in the tube 4 in a particular order.

The assembly 2 is used to draw blood from a patient as shown in FIG. 1. The finger stick is made with the crimped end 6 of the tube 4, and blood 20 is drawn into the tube 4 by capillary action, as indicated by arrows B, while air is expelled from the tube 4 as indicated by arrows A. The tube bore 16 is precoated with an anticoagulant such as heparin so that the blood sample is anti coagulated as it enters the tube 4. The tube 4 is preferably equipped with a visible indicium 23, such as one or more bands which indicate the proper fill level of the blood sample.

After the tube 4 is properly filled with anti coagulated blood, the plug 12 is pushed into the tube 4, and the tube 4 is inverted as shown in FIG. 2 so that the assembly 2 can be centrifuged to separate the components of the blood sample 20 gravimetrically with the heavier components moving toward the plug 12 and the lighter of the components moving toward the crimped end 6 of the tube 4. During the centrifugation step, the markers 14, 16, 18, etc., will settle gravimetrically into the centrifuged sample as shown in FIG. 2. The marker 18 will be spaced apart from the plug 12 by a zone 22, and therefore all of the components in the sample between the marker 18 and the plug 12 and thus in the zone 22, will necessarily have a density which is greater than the density of the marker 18. Likewise, the sample components which are interposed between markers 14–16, and 16–18 have densities which are between the densities of the respective markers. The centrifuged sample components will therefore be gravimetrically separated, and the markers 14, 16, 18, etc., will be operable to demarcate the gravimetric boundaries of the separated sample components in the tube 4. In the case of the blood sample, the red cells, being the most dense, will settle nearest the plug 12, the white cells and platelets will settle on top of the red cells, and the plasma, which is primarily water, will settle on top of the white cells and platelets. The red cell layer is formed from red cells which have densities that vary due to the variation in the water content thereof. Thus, the red cells form a density gradient within the centrifuged blood sample. The markers 14, 16, 18, etc., can have respective densities that will cause them all to gravitate to separate locations, all of which are within the red cell layer; or some of which are within the red cell layer and others of which are within the white cell and platelet layers, or wherever else the artisan wishes them to settle. Thus, the markers can be used to demarcate gravimetric boundaries of a particular subset or subsets of blood cells.

After the sample has been centrifuged, the tube 4 can be cut as at 5, as shown in FIG. 3, so as to remove the crimped end 6 therefrom. The cut 5 will be made as close as possible to the portion of the sample containing the layers to be harvested. Typically, the cut 5 will be made near the bottom of the plasma layer of the blood sample so as to remove the plasma en masse from the centrifuged blood sample. In order to harvest the desired cell layer or layers from the sample tube 4, one pierces the elastomeric stopper 12 with a cannula 24, as shown in FIG. 3, where after one injects air or a liquid (which liquid is preferably, but not necessarily, immiscible with the sample being tested) into the tube 4 through the cannula 24. When the tube 4 is a capillary tube, and the sample being harvested is anti coagulated whole blood, the fluid injected into the tube 4 can be air. An upwardly expanding column of air 26 is thus created in the tube 4 below the cells in the zone 22. The centrifuged components, including the cells in the zone 22 are pushed, without being disrupted by the air column 26, toward the cut end 5 of the tube 4. The contents of the tube 4 will thus be sequentially expelled from the tube 4 through the cut end 5 thereof. In order to harvest the components between the markers 14 and 16, one need merely eject the marker 14 from the tube 4 and then eject the succeeding component fraction into a container or onto a slide, or the like, until the marker 16 reaches the cut end 5 of the tube 4. The component fraction between the markers 16 and 18 can likewise be isolated and harvested, as can the component fraction between the air column 26 and the marker 18.

It will be readily appreciated that this invention is applicable to the isolation and harvesting of densimetrically differentiated constituent fractions of any liquid or liquefied material mixture which contains such constituent fractions. As many markers as are necessary to isolate the target fraction or fractions may be incorporated into the sample tube. Materials other than blood can be differentiated and harvested through the use of this invention. When capillary tubes are used, the fluid injected into the tube can typically be air, and when larger sample tubes are used, the injected fluid can be a liquid which is preferably immiscible with the material being harvested. In order to highlight the markers, they may be formed with colored or fluorescent plastics.

Since many changes and variations of the disclosed embodiment of the invention may be made without departing from the inventive concept, it is not intended to limit the invention otherwise than as required by the appended claims.

What is claimed is:

1. A method for harvesting constituent components from a multi-constituent material which includes gravimetrically separable constituent components, said method comprising the steps of:

a) providing a sample of the material in a sampling tube;
   b) providing a plurality of gravimetrically separable markers in the sampling tube;
   c) centrifuging the sampling tube so as to form a column of gravimetrically separated constituent component layers in the tube, so as to embed the markers in the column whereby each of the material constituent components in said column thereof is separated from an adjacent material constituent component by a respective one of the markers; and d) expressing a target material constituent component layer which lies between adjacent markers through an opening in the tube so as to harvest said target material constituent component layer from the tube.

2. The method of claim 1 wherein said expressing step is performed by pushing at least one of said markers against an end of said target constituent material component layer so that said target constituent material component layer is pushed through said tube opening.

3. The method of claim 2 wherein said expressing step is performed by injecting a fluid into said sampling tube.

4. The method of claim 1 wherein said markers are discs which are operable to form a seal with an internal side wall of the sampling tube.

5. A method for harvesting a target subset of erythrocyte cells from a sample of anticoagulated whole blood, said method comprising the steps of:

a) providing a sample of the blood in a sampling tube;

b) providing a plurality of gravimetrically separable marker discs in the sampling tube, said discs being sized so as to provide a seal with an internal side wall of the sampling tube;

c) centrifuging the sampling tube so as to form a column of erythrocyte cells in the tube, and so as to embed the markers in the erythrocyte column whereby gravimetrically distinct subsets of erythrocytes in said column thereof are separated from each other by a respective one of the markers; and d) injecting a fluid into said sampling tube so as to express the target subset of erythrocytes which lies between adjacent markers through an opening in the tube so as to harvest said target subset of erythrocytes from the tube.

6. The method of claim 5 wherein said fluid is injected into said tube through one end of said tube.

7. The method of claim 5 further comprising the step of cutting the sampling tube at a location adjacent to one end of the target subset of erythrocytes to form a cut opening in the sampling tube through which the target subset of erythrocytes is expressed.

* * * * *